United States Patent [19]
Berchem

[11] Patent Number: 4,955,912
[45] Date of Patent: Sep. 11, 1990

[54] JOINT PROSTHESIS

[75] Inventor: Rütger Berchem, Essen, Fed. Rep. of Germany

[73] Assignee: Metalpraecis Berchem+Schaberg Gesellschaft fur Metallformgebung mit Beschrankter Haftung, Gelsenkirchen-Uckendorf, Fed. Rep. of Germany

[21] Appl. No.: 276,187

[22] Filed: Nov. 23, 1988

[30] Foreign Application Priority Data

Nov. 28, 1987 [DE] Fed. Rep. of Germany ....... 3740438

[51] Int. Cl.$^5$ .............................................. A61F 2/30
[52] U.S. Cl. ........................................ 623/18; 623/23
[58] Field of Search ...................... 623/16, 18, 20, 22, 623/23

[56] References Cited

U.S. PATENT DOCUMENTS

| 4,514,865 | 5/1985 | Harris | 623/23 |
| 4,536,894 | 8/1985 | Galante et al. | 623/16 |
| 4,722,870 | 2/1988 | White | 623/16 |

Primary Examiner—David J. Isabella
Attorney, Agent, or Firm—Herbert Dubno

[57] ABSTRACT

A joint prosthesis, especially for a hip joint has a metal shaft receivable in the marrow cavity of the bone, a closure plate at the upper end of the shaft, and a formation adapted to form the ball joint. The underside of the plate and the shaft along its length are provided with a layer of synthetic bone material which is of greater thickness in the region of the plate and adjoining the plate, corresponding to the greater stress region of the bone, than along the shank remote from the plate.

6 Claims, 2 Drawing Sheets

JOINT PROSTHESIS

FIELD OF THE INVENTION

My present invention relates to a joint prosthesis, especially for a hip joint and, more particularly, to the member of an artificial joint which is intended to be mounted in the femur of the patient. Specifically, the invention relates to a member for an artificial hip joint which comprises a shaft receivable in the marrow cavity of the femur.

BACKGROUND OF THE INVENTION

In joint prostheses or artificial joints it is common to insert one member of the artificial joint into a bone forming that joint. In the case of an artificial hip joint, that member can have a shaft which is forced into the marrow cavity of the femur and is provided at its upper end with a fitting adapted to receive a ball of the joint or forming the ball itself. Between the ball and the shaft, a closure plate can be provided which is adapted to close off the open section of the neck of the femur which may be cut away upon removal of the femur head to accommodate the artificial joint.

The shaft and the plate are generally composed of metal and it has been proposed to provide at least the shaft with a coating or layer of an artificial bone material, sometimes referred to as synthetic bone or as artificial bone replacement material.

The shaft and the closure plate can be formed together with the ball-forming or ball-connecting member in one piece from a titanium alloy or a cobalt-chromium alloy.

The joint prosthesis can be made by forging, casting and/or machining operations.

The layer of the so-called synthetic bone material is generally sintered on the metal body. The synthetic bone material can have a ceramic character and generally comprises at least one artificial apatite in the form of hydroxyapatite $Ca_5OH(PO_4)_2$.

The material can be applied in a multilayer configuration and the various layers can be composed of different materials.

The layer of the synthetic bone material is not only highly compatible with natural bone tissue, but has a certain porosity.

The shaft which is inserted into the marrow cavity can be provided with ribs running in the direction of insertion so as to increase the surface area of the layer exposed to the bone tissue. Furthermore, the metallic surface of the shaft and the closure disc can be treated by spark-discharge erosion to form micropits or roughening formations which promote attachment of the synthetic bone material thereto.

A joint prosthesis as thus formed and constituted is not cemented into or onto the bone as is the case with some artificial joints, but rather, after insertion, becomes permanently attached by a growth of the natural bone tissue within the cortex of the bone into the layer. The prosthetic joint of course must have sufficient alternating bending strength and should be sufficiently strong as to resist rupture under even the most extreme conditions of supporting the body.

In practice, the synthetic bone layer has been applied to the metal prosthesis body with a uniform thickness over the entire coated surface thereof. In practice, moreover, it has been found that the growth of natural bone material into the layer and hence the attachment of the prosthesis to the bone is unsatisfactory. Investigations have shown that this unexpected phenomenon appears to be a result of the fact that movements of the patient cause higher stresses on the bone and the connection between the bone and the prosthetic member in the region of the closure plate than elsewhere along the shaft remote from the closure plate. In other words the more highly stressed region of the prosthetic member and the bone and the more highly loaded tissue at the closure plate and directly adjoining same along the shaft does not permit as effective growth of the bone tissue into the layer and as effective bonding of the prosthesis in this region as in regions of reduced loading and less stress more remote from the plate.

The phenomenon, therefore, which has been recognized as a lack of effective bonding uniformly between the bone tissue and the implant, has been traced to the sharp differences in loading along the shank or shaft of the implant. This is especially the case with hip prostheses.

OBJECTS OF THE INVENTION

It is, therefore, the principal object of the present invention to provide an improved prosthesis adapted to be inserted into the marrow cavity of a bone, whereby these drawbacks are avoided.

Another object of the invention is to provide an improved joint prosthesis, especially for a hip joint, which has improved attachment of the implant in the bone tissue, i.e. which will permit bone tissue to grow into the implant more effectively in spite of the fact that the bone and the implant are subjected to greater stress in some regions than in others.

Still another object of this invention is to provide an improved hip joint which is more effectively fixed in the bone.

SUMMARY OF THE INVENTION

These objects and others which will become apparent hereinafter are attained, in accordance with the present invention by providing, in a prosthesis of the type described and especially a hip joint prosthesis, wherein the shaft is provided with a layer of the synthetic bone material as has been described, that this layer has a greater thickness in the higher loading and higher stress regions of the bone than the thickness in the regions of reduced loading. Specifically the greater thickness should be a multiplicity of times greater than the lesser thickness.

More specifically, a joint prosthesis of the invention can comprise:

an elongated shaft composed of metal and receivable in a marrow cavity of a bone adapted to form one side of a joint;

a closure plate of metal on one end of the shaft and adapted to close an end of the bone, the plate having a surface projecting outwardly at a junction between the plate and the shaft;

ball-joint means on the closure plate adapted to engage in a socket formation; and a layer of synthetic bone material covering at least the shaft for enabling bone tissue of the bone into which the shaft is inserted to grow into the layer, the layer having a greater thickness in regions of the shaft corresponding to more highly loaded regions of the bone and a lesser thickness in regions of the shaft corresponding to lesser loaded regions of the bone, the greater thickness being a multiplicity of times greater than the lesser thickness.

Specifically, wherein the joint is a hip prosthesis in which the bone is a femur, the ball-joint means is adapted to form an artificial head of the femur, the closure plate is adapted to span across the neck of the femur, and the layer has the greater thickness adjacent the plate and the lesser thickness remote from the plate.

According to a feature of the invention, the reduced thickness layer has a thickness of about 0.2 mm which can correspond to the thickness of the layer which has been applied uniformly in the past to the implant. The thickness of the layer in the loaded regions, however, should be 10 to 30 times greater than this thickness.

In general it is sufficient to apply the greater thickness of the layer over a region of the shaft extending several centimeters from the closure plate and, indeed, it has also been found to be advantageous to provide other regions of high loading with the greater thickness layer as well, e.g. the surface of the plate turned toward the bone tissue, the underside of the plate.

The regions in which higher loading exists can be determined for each patient in which the joint prosthesis is to be implanted by techniques which have been developed for determining stresses in bone, namely with X-ray images and the aid of modern computer supported stress mechanics evaluation. The joint prosthesis can be fabricated to suit each particular patient, although it is possible to provide the joint prosthesis in a standard form utilizing the knowledge of the usual stress regions of the bone for the average patient. In either case there is a marked improvement of the attachment of the prosthesis to the bone tissue by comparison with systems in which the layer of synthetic bone which is applied in a uniform thickness over the entire shaft of the prosthesis.

It has been found to be advantageous, moreover, to provide a stepless transition in thickness between the layer in the more highly loaded regions and the layer in the regions of reduced loading of the bone.

With the joint prosthesis of the present invention there is a highly intense bonding of the prosthesis in the bone tissue even in the very highly stressed regions and the bonding is effected more rapidly in these regions in spite of the greater stresses to which the prosthesis and the bone tissue may be subject.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
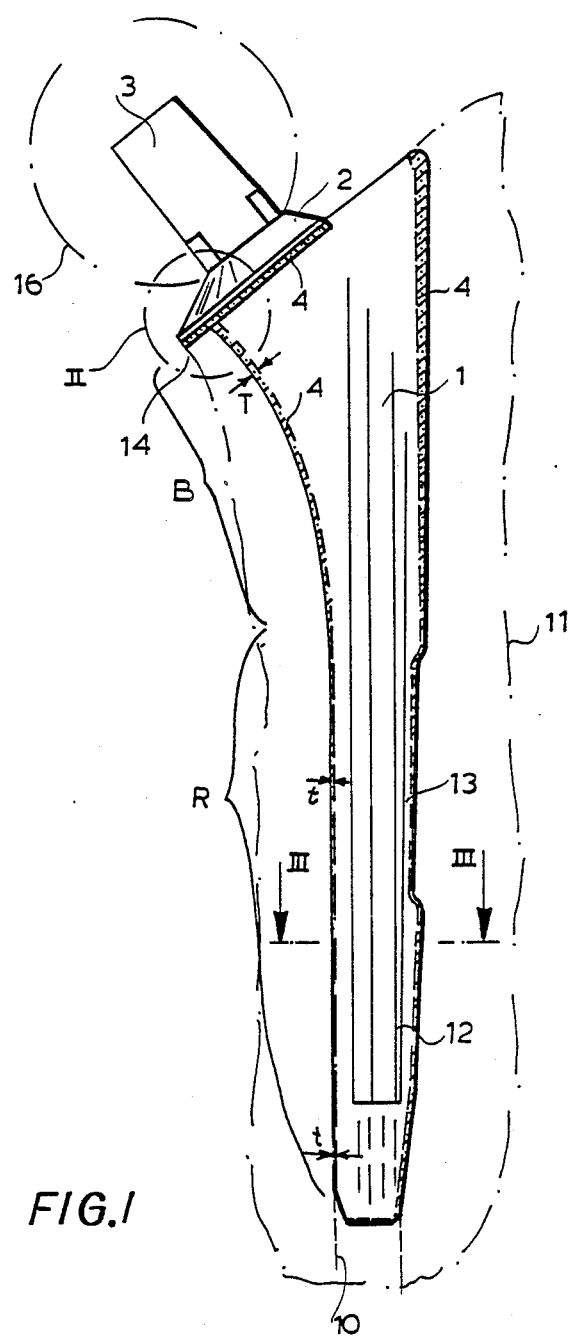
FIG. 1 is a diagrammatic view in which the relationship between the parts of the prosthesis have been shown and in which the bone and marrow cavity have been illustrated also in highly diagrammatic form and in dot-dash lines.
Figure 2:
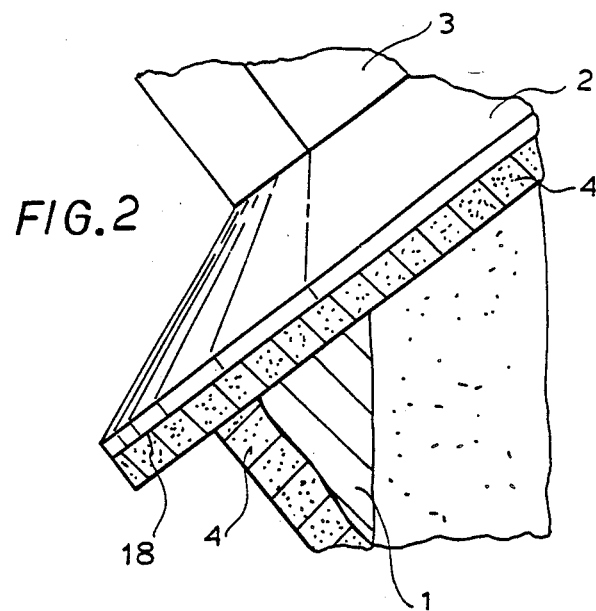
FIG. 2 is an elevational view, with the layer of synthetic bone material broken away, forming a detail of the region III of FIG. 1.
Figure 3:
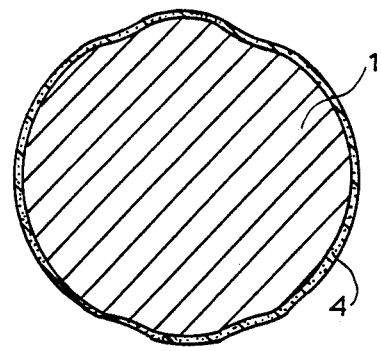
FIG. 3 is a cross-sectional view taken along the line III—III of FIG. 1.

The hip joint prosthesis illustrated by way of example in FIGS. 1-3 has a shaft 1 which can be driven into the marrow cavity 10 of a femur 11 shown only in dot-lines in the drawing. The shaft 1 may have ribs or other formations 12 and recessed portions 13 to increase the attachment area and promote anchoring of the shaft in the bone.

At its upper end, closing a sectioned neck 14 of the femur, the head of which has been surgically removed, is a closure plate 2 from which a ball connecting part 3 projects. The ball 16 of the joint has also been shown in dot-dash lines.

The shaft 1 with the closure plate 2 and the ball connecting part 3 are composed of metal, e.g. a titanium or cobalt-chromium alloys has been described.

The shaft 1 and other parts of the prosthesis which may contact bone tissue, are formed with a layer 4 of synthetic bone material which can be applied after the metal surface has been subjected to spark erosion roughening and sintered in place. The preferred synthetic bone material forming the layer 4 is hydroxyapatite.

It will be apparent that the shaft 1 inserted into the bone and especially the underside of the closure plate 2, during movement of the patient, especially in the case of a hip prosthesis, can be subjected to vastly different stresses and loading. A highly loaded region B at a region R of reduced loading ca thus be distinguished.

From FIGS. 1 and 2 it can be seen that the layer 4 of the synthetic bone material, according to the invention varies in thickness along the length of the shaft and, specifically, as a thickness T in the region of greater stress which is some 10 to 30 times greater than the thickness t in the regions of reduced loading. The thickness t can be 0.2 mm. It also may be seen from the drawing that the region of greater thickness may extend from the plate 2 downwardly over a length of several centimeters and that there may be a continuous transition in thickness between the two regions.

The downwardly turned surface 18 of the plate 2, i.e. the surface turned toward the bone tissue of the neck of the femur, may also be provided with the layer to the thickness T.

I claim:

1. A metallic prosthesis, comprising: an elongated shaft having an outer bone engaging surface, said outer surface being divided into proximal and distal regions wherein respective regions terminate in opposite proximal and distal ends, said shaft adapted to be receivable in a marrow cavity at one end of a femur;
   a collar disposed on a proximal end of said shaft and adapted to seat on a resected surface of the femur, said collar having a lower bone engaging surface extending radially outwardly of the shaft;
   a ball-joint means disposed on a surface opposite said bone engaging surface, said ball-joint means adapted to pivotally engage an acetabular member; and
   a layer of synthetic bone material coating said shaft, said layer having a greater thickness in the proximal region and a lesser thickness in the distal region of the shaft, said lesser thickness being about 0.2 mm and said greater thickness being about 10–30 times greater than said lesser thickness wherein said bone material enables new bone tissues to grow into said layer along the length of the shaft.

2. The metallic prosthesis defined in claim 1 wherein said lower bone engaging surface is coated with said synthetic bone material.

3. The metallic prosthesis defined in claim 2 wherein the greater thickness of said layer decreases continuously through the region proximal to said collar toward the distal end of said shaft and merges steplessly with the lesser thickness of said layer.

4. The metallic prosthesis defined in claim 1 wherein the synthetic bone material is hydroxyapatite and is sintered to said shaft, said shaft being of a material selected from the group consisting of titanium and cobalt-chromium alloy, and being formed in one piece with said collar.

5. A metallic prosthesis, comprising: an elongated shaft having an outer bone engaging surface, said outer surface being divided into proximal and distal regions wherein respective regions terminate in opposite proximal and distal ends, said shaft adapted to be receivable in a marrow cavity at one end of a bone;

a collar disposed on a proximal end of said shaft and adapted to seat on a resected surface of the bone, said collar having a lower bone engaging surface extending radially outwardly of the shaft;

a ball-joint means disposed on a surface opposite said bone engaging surface, said ball-joint means adapted to pivotally engage an acetabular member; and a layer of synthetic bone material coating said shaft, said layer having a greater thickness in the proximal region and a lesser thickness in the distal region of the shaft, said lesser thickness being about 0.2 mm and said greater thickness being about 10–30 times greater than said lesser thickness wherein said bone material enables new bone tissues to grow into said layer along the length of the shaft.

6. The metallic prosthesis defined in claim 5 wherein said lower bone engaging surface is coated with said synthetic bone material.

* * * * *